(12) United States Patent
Cable, II et al.

(10) Patent No.: US 11,806,227 B2
(45) Date of Patent: Nov. 7, 2023

(54) SULCUS IMPLANTS AND METHODS OF USING THE SAME

(71) Applicants: SpyGlass Pharma, Inc., Aliso Viejo, CA (US); The Regents of the University of Colorado, a body corporate, Denver, CO (US)

(72) Inventors: Craig Alan Cable, II, Aliso Viejo, CA (US); Malik Y. Kahook, Denver, CO (US); Glenn R. Sussman, Aliso Viejo, CA (US); James R. Dennewill, Aliso Viejo, CA (US)

(73) Assignees: SpyGlass Pharma, Inc., Aliso Viejo, CA (US); The Regents of the University of Colorado, a body coporate, Denver, CO (US)

( * ) Notice: Subject to any disclaimer, the term of this patent is extended or adjusted under 35 U.S.C. 154(b) by 0 days.

(21) Appl. No.: 17/954,631

(22) Filed: Sep. 28, 2022

(65) Prior Publication Data
US 2023/0020167 A1    Jan. 19, 2023

Related U.S. Application Data

(63) Continuation of application No. PCT/US2021/057104, filed on Oct. 28, 2021.

(60) Provisional application No. 63/108,675, filed on Nov. 2, 2020, provisional application No. 63/106,849, filed on Oct. 28, 2020, provisional application No. 63/106,847, filed on Oct. 28, 2020.

(51) Int. Cl.
*A61F 2/14* (2006.01)
*A61F 2/16* (2006.01)

(52) U.S. Cl.
CPC ............ *A61F 2/147* (2013.01); *A61F 2/1605* (2015.04); *A61F 2002/169* (2015.04); *A61F 2002/1682* (2015.04); *A61F 2002/1689* (2013.01); *A61F 2002/16901* (2015.04)

(58) Field of Classification Search
None
See application file for complete search history.

(56) References Cited

U.S. PATENT DOCUMENTS

| | | | |
|---|---|---|---|
| 5,047,051 A | 9/1991 | Cumming | |
| 2001/0016771 A1 | 8/2001 | Cumming | |
| 2003/0114927 A1* | 6/2003 | Nagamoto | ............ A61F 2/1613 623/6.37 |
| 2005/0125058 A1 | 6/2005 | Cumming et al. | |

FOREIGN PATENT DOCUMENTS

| | | |
|---|---|---|
| WO | 0117461 A1 | 3/2001 |

OTHER PUBLICATIONS

Patent Cooperation Treaty, International Search Report and Written Opinion, International Application No. PCT/US2021/057104, dated Feb. 24, 2022, 13 pages.

* cited by examiner

*Primary Examiner* — Leslie Lopez
(74) *Attorney, Agent, or Firm* — Polsinelli PC

(57) ABSTRACT

This disclosure provides ophthalmic implants such as sulcus implants which can comprise one or more drug delivery devices. Further provided herein are methods of using the drug delivery ophthalmic devices described herein for implantation into a subject's eye, e.g., into an eye's ciliary sulcus or capsular bag.

20 Claims, 10 Drawing Sheets

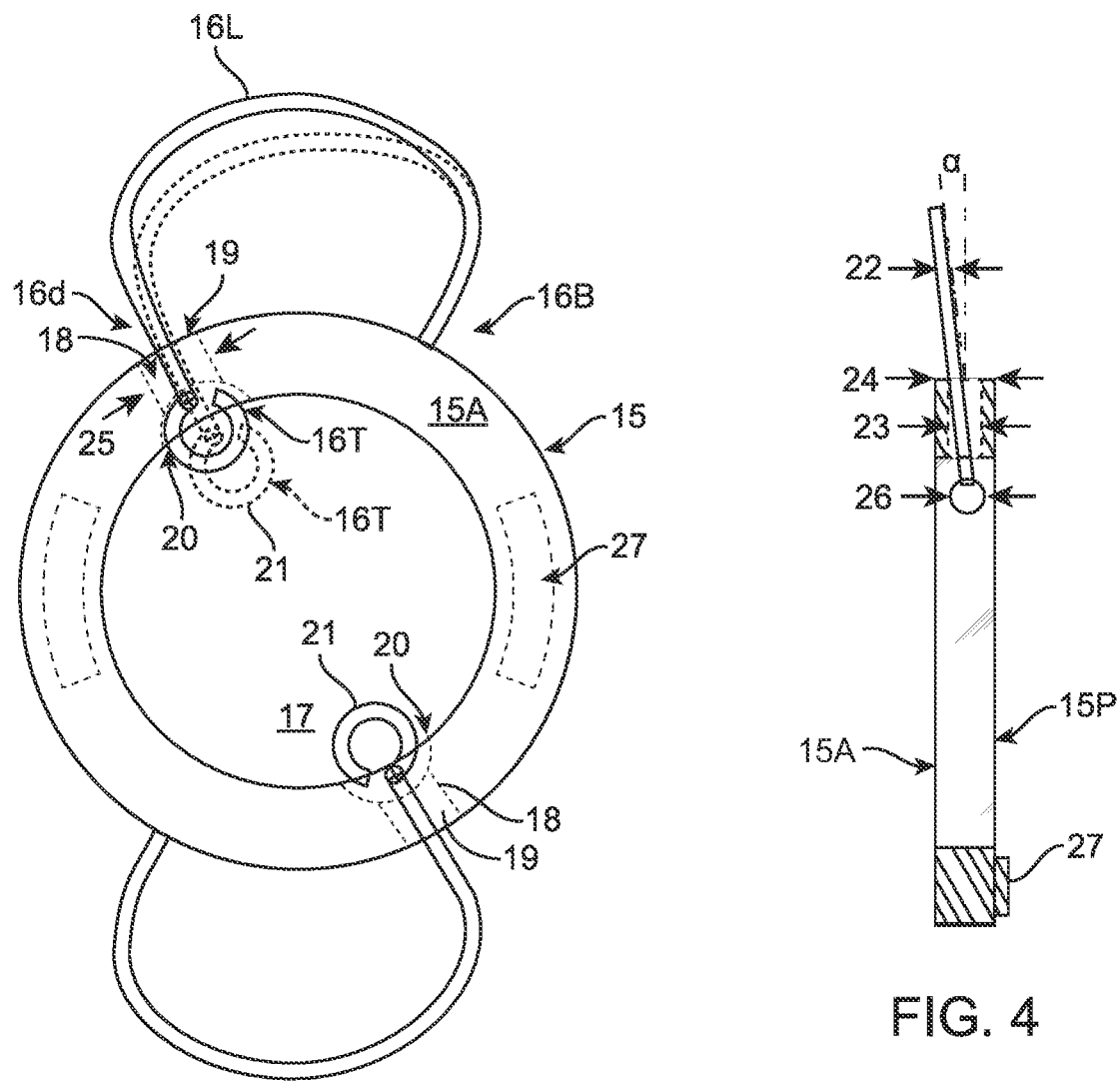
FIG. 3
FIG. 4
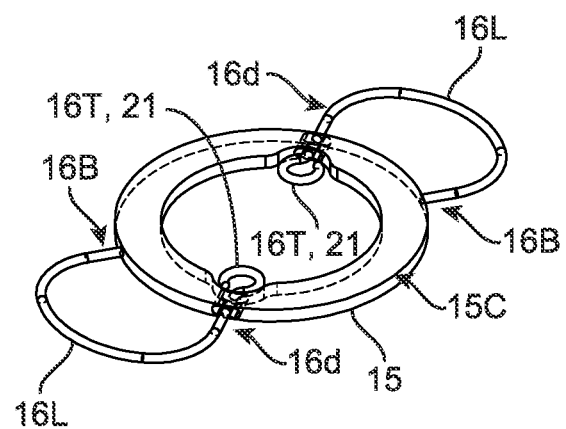
FIG. 5

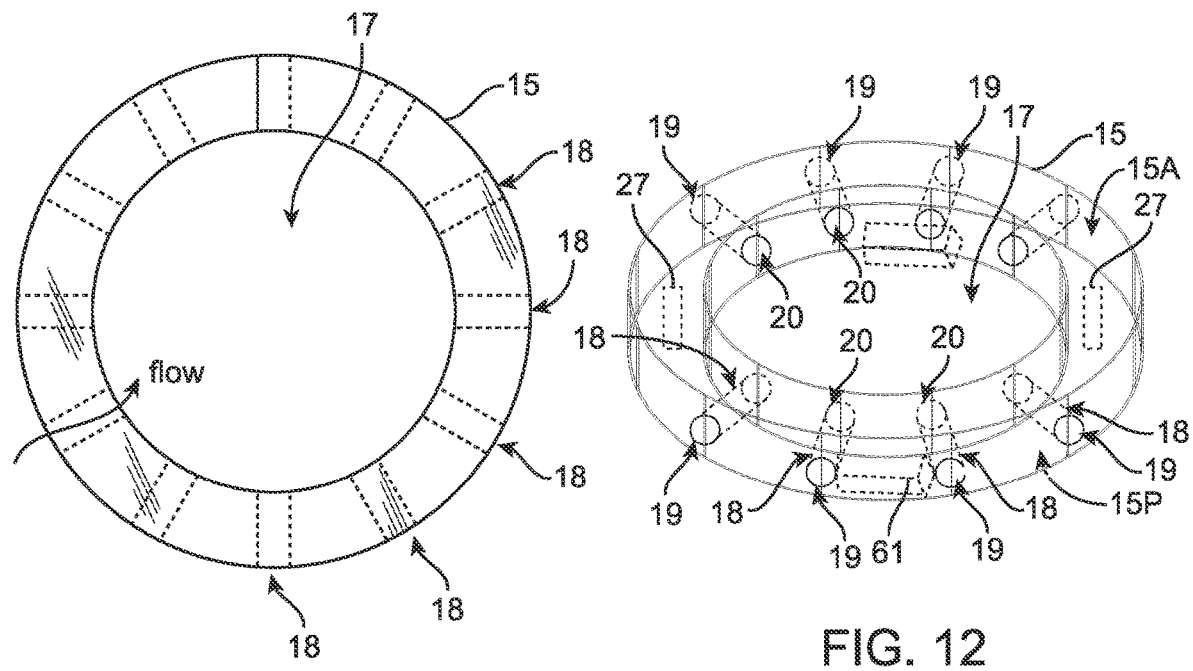
FIG. 11
FIG. 12
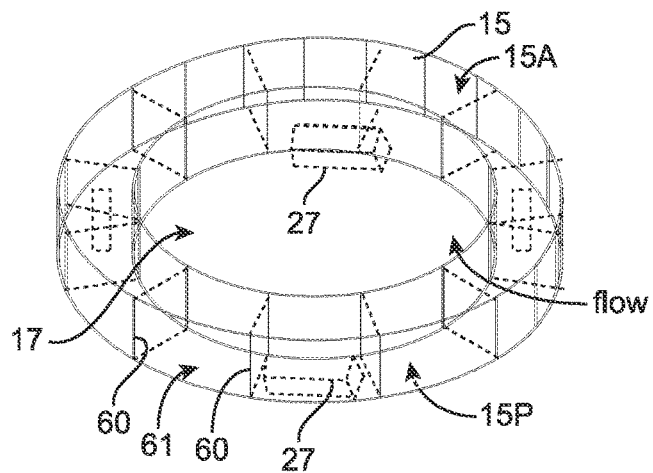
FIG. 13
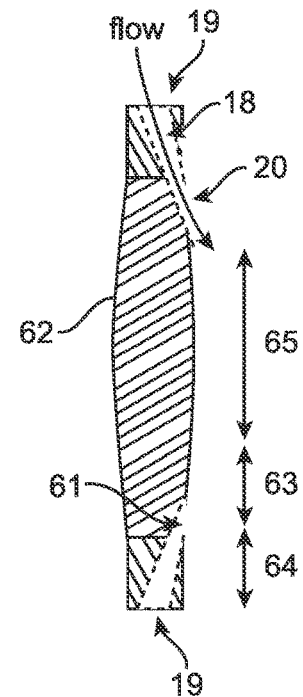
FIG. 14

SULCUS IMPLANTS AND METHODS OF USING THE SAME

CROSS-REFERENCE

This application is a continuation of International Application No. PCT/US2021/057104, filed Oct. 28, 2021, which claims the benefit of U.S. Provisional Application No. 63/106,847, filed Oct. 28, 2020, U.S. Provisional Application No. 63/106,849, filed Oct. 28, 2020, and U.S. Provisional Application No. 63/108,675, filed Nov. 2, 2020, which applications are incorporated herein by reference in their entireties for all purposes.

BACKGROUND OF THE INVENTION

Conventional intraocular implants can be limited in terms of their manufacturability and in their ability to provide therapeutic benefit without damaging eye tissue once implanted. Hence, there is an unmet need for intraocular implants that provide improved safety and lower tissue impairment during use as well as improved manufacturability.

SUMMARY OF THE INVENTION

Provided herein are intraocular implants that can be implanted into a subject's eye. In some instances, provided herein are intraocular implants for implantation into a ciliary sulcus or capsular bag of a subject's eye.

In various embodiments, the ocular implants comprise a ring or partial ring 15 comprising a first material and configured for implantation into an eye of a subject, the ring or partial ring characterized by an outer circumferential surface, an inner wall, and a central aperture 17; and a closed loop haptic 16, 16C, 16L, 43, 46 comprising a second material and attached to the ring or partial ring at a haptic first end 16d, 41, 45 and at a haptic second end 16d, 42, 44, wherein the first material and the second material have different chemical compositions and the ring or partial ring is more rigid than the closed loop haptic.

In some aspects, at the conditions present in the eye following implantation, the ring or partial ring retains its shape and the closed loop haptic deforms. In other aspects, at an applied force of 100 mN, the ring or partial ring retains its shape and the closed loop haptic deforms. In further aspects, at an applied force of 10 mN, the ring or partial ring retains its shape and the closed loop haptic deforms.

In certain aspects, the ocular implants comprise a plurality of closed loop haptics.

In some aspects, the haptic first end is flexibly connected to the ring at the haptic first end such that the closed loop haptic is deformable by forces applied by tissues into which the implant is implanted.

In other aspects, a portion of the closed loop haptic passes through a hole 18, 49, 50, 84 of the ring and into the central aperture to form a grasping feature 21, 85.

In some aspects, the haptic second end is flexibly connected to the ring at the haptic second end such that the closed loop haptic is deformable by forces applied by tissues into which the implant is implanted.

In some embodiments, the closed loop haptic is configured such that the haptic first end, the haptic second end, or a combination thereof is disposed within a recess of the ring 15. In other aspects, the haptic first end is attached to the ring by mechanically fixing the haptic first end to the ring, over-molding the haptic first end with the ring, fusing the haptic first end to the ring, attaching the haptic first end to the ring via a heat shrink attachment, attaching the haptic first end to the ring via an adhesive, or a combination thereof.

In certain embodiments, the haptic second end is attached to the ring by mechanically fixing the haptic second end to the ring, over-molding the haptic second end with the ring, fusing the haptic second end to the ring, attaching the haptic second end to the ring via a heat shrink attachment, attaching the haptic second end to the ring via an adhesive, or a combination thereof.

In some aspects, the first material is a biocompatible material and the second material is a biocompatible material. In other aspects, the first material is a first polymer and the second material is a second polymer. In certain aspects, the first material is selected from the group consisting of a silicone, acrylic, hydroxyethyl methacrylate (HEMA), polyethylmethacrylate (PEMA), and polyethylacrylate (PEA), or any combination thereof.

In some embodiments, the second material is an elastomer. In other embodiments, the second material is selected from the group consisting of a polymethyl methacrylate (PMMA), polyvinylidene difluoride (PVDF), Polypropylene (PP) and Polyethersulfone (PES) or any combination thereof.

In various embodiments, the ocular implants comprise a ring or partial ring 15 configured for implantation into an eye of a patient, the ring characterized by an outer circumferential surface, an inner wall, and a central aperture 17; and a haptic 16, 16L, 43, 46 connected to the ring at a haptic first end 16d, 41, 43 and a haptic second end 16d, 42, 44, wherein the haptic is flexibly connected to the ring at the haptic first end such that the haptic is deformable by forces applied by tissues into which the implant is implanted.

In some embodiments, the haptic is flexibly connected to the ring at the haptic second end such that the haptic is deformable by forces applied by tissues into which the implant is implanted.

In other aspects, the haptic is configured such that the haptic first end, the haptic second end, or a combination thereof is disposed within a recess 37, 52, 53 of the ring 15.

In certain embodiments, the ring comprises a hole 18, 36, 47, 48, 49, 50, 52, 53 communicating from an opening 19, 51, 56, 57 in the outer circumferential surface toward the inner wall. In some aspects, the haptic second end 16d, 42, 44 is slidably disposed within the hole 18, 36, 48, 50, 52.

In various aspects, the ocular implants are configured for implantation into a posterior chamber and ciliary sulcus of an eye of a subject.

In some embodiments, the haptic second end is flexibly connected to the ring at the haptic second end such that the haptic is deformable by forces applied by tissues into which the implant is implanted.

In certain aspects, the haptic second end is attached to the ring by mechanically fixing the haptic second end to the ring, over-molding the haptic second end with the ring, fusing the haptic second end to the ring, attaching the haptic second end to the ring via a heat shrink attachment, attaching the haptic second end to the ring via an adhesive, or a combination thereof.

In various aspects, the present disclosure provides ocular implants configured for implantation into an eye of a subject, the ocular implants comprising: a ring 15 configured for implantation into the eye of the subject, the ring characterized by an outer circumferential surface, an inner wall, and a central aperture 17; a haptic 16, 16L, 43, 46 connected to the ring at a haptic first end 16d, 41, 45 and a haptic second end 16*d*, 42, 44, wherein the ring comprises a hole 18, 49, 50, communicating from an opening 19, 51 in the outer circumferential surface toward the inner wall; and the haptic second end 16*d*, 42, 44 is disposed within the hole 18, 48, 50, 52 and is slidably disposed within the hole, whereby the haptic is deformable by forces applied by tissues into which the implant is implanted may operate to force the haptic second end into the hole 18, 48, 50, 52.

In various aspects, the present disclosure provides ocular implants configured for implantation in a posterior chamber and ciliary sulcus of an eye of a subject, the ocular implants comprising: a ring 15 configured for implantation in the posterior chamber of the eye of the subject, the ring characterized by an outer circumferential surface, an inner wall, and a central aperture 17; a haptic 16, 16L, 43, 46 connected to the ring at a haptic first end 16*d*, 41, 45 and a haptic second end 16*d*, 42, 44, wherein the ring comprises a hole 18, 49, 50, communicating from an opening 19, 51 in the outer circumferential surface toward the inner wall; and the haptic second end 16*d*, 42, 44 is disposed within the hole 18, 48, 50, 52 and is slidably disposed within the hole, whereby the haptic is deformable by forces applied by tissues into which the implant is implanted may operate to force the haptic second end into the hole 18, 48, 50, 52.

In some aspects, the haptic second end 16*d*, 42, 44 comprises a haptic distal tip 16T, having a larger cross section than a remainder of the haptic second end 16*d*, 42, 44.

In other embodiments, the haptic second end 16*d*, 42, 44 comprises a haptic distal tip 16T, having a larger cross section than a remainder of the haptic second end 16*d*, 42, 44, and the thru-hole 18, 36, 48, 50 has a bore with a cross section smaller than the haptic distal tip 16T, whereby the haptic second end is inhibited or prevented from removal from the thru-hole.

In some aspects, the ocular implants further comprise a grasping feature 21 disposed on the haptic second end 16*d*, 42, 44, said grasping feature configured for engagement of a grasping tool.

In other aspects, the hole 18, 50 communicating from the opening 19, 51 in the outer circumferential surface toward the inner wall is a through hole communication to an opening 20, 56 in the inner wall of the ring, and the haptic second end 16*d*, 42, 44 comprises a haptic distal tip 16T, having a larger cross section than a remainder of the haptic second end 16*d*, 42, 44, and said haptic distal tip 16T is disposed in the central aperture 17.

In further embodiments, the haptic first end 16*d*, 41, 45 comprises a haptic distal tip 16T, having a larger cross section than a remainder of the haptic first end 16*d*, 41, 45.

In some aspects, the haptic first end 16*d*, 41, 45 comprises a haptic distal tip 16T, having a larger cross section than a remainder of the haptic first end, and the thru-hole 18, 47, 49 has a bore with a cross section smaller than the haptic distal tip 16T, whereby the haptic first end is inhibited or prevented from removal from the thru-hole.

In other embodiments, the ocular implants, further comprise a grasping feature 21 disposed on the haptic first end 16*d*, 41, 45, said grasping feature configured for engagement of a grasping tool.

In certain aspects, the hole 18, 49, communicating from the opening 19, 51 in the outer circumferential surface toward the inner wall is a through hole communication to an opening 20, 57 in the inner wall of the ring, and the haptic first end 16*d*, 41, 45 comprises a haptic distal tip 16T, having a larger cross section than a remainder of the haptic first end, and said haptic distal tip 16T is disposed in the central aperture 17.

In some embodiments, the hole 18, 52, 53, 49, 50 is radially oriented within the ring. In other embodiments, the hole 18, 52, 53, 49, 50 is chordally oriented within the ring. In further embodiments, the hole 18, 49, 50 is a thru-hole communicating with an opening in the inner wall of the ring or an anterior surface of the ring. In additional elements, the hole 18, 52, 53 is a blind hole terminating with the ring.

In some aspects, the haptic first end is flexibly connected to the ring at the haptic second end such that the haptic is deformable by forces applied by tissues into which the implant is implanted.

In certain aspects, the haptic first end is attached to the ring by mechanically fixing the haptic first end to the ring, over-molding the haptic first end with the ring, fusing the haptic first end to the ring, attaching the haptic first end to the ring via a heat shrink attachment, attaching the haptic first end to the ring via an adhesive, or a combination thereof.

In other aspects, the ring comprises a first biocompatible material and the haptic comprises a second biocompatible material.

In some embodiments, the first biocompatible material and the second biocompatible material have different chemical compositions and the ring or partial ring is more rigid than the haptic.

In some aspects, at the conditions present in the eye following implantation, the ring or partial ring retains its shape and the closed loop haptic deforms. In some embodiments, an applied force of 100 mN, the ring or partial ring retains its shape and the closed loop haptic deforms. In other embodiments, at an applied force of 10 mN, the ring or partial ring retains its shape and the closed loop haptic deforms.

In certain embodiments, the first biocompatible material is a first polymer and the second biocompatible material is second polymer. In some aspects, the first biocompatible material is selected from the group consisting of a silicone, acrylic, hydroxyethyl methacrylate (HEMA), polyethylmethacrylate (PEMA), and polyethylacrylate (PEA), or any combination thereof.

In some aspects, the second biocompatible material is an elastomer. In certain embodiments, the second biocompatible material is selected from the group consisting of a polymethyl methacrylate (PMMA), polyvinylidene difluoride (PVDF), Polypropylene (PP) and Polyethersulfone (PES) or any combination thereof.

In some embodiments, the ocular implants further comprise a drug delivery structure.

In certain aspects, the ocular implants further comprise a lens 34 disposed within the central aperture 17.

In various embodiments, the ocular implants comprise: first and second arcuate drug delivery structures 70 configured for implantation into an eye of a subject, the first and second arcuate drug delivery structures having an outer contour 70C configured for installation in the sulcus, the first and second arcuate drug delivery structures comprising a therapeutic agent configured to treat a condition or disorder of the eye of the subject; and first and second biasing members 71 connecting the first and second arcuate drug delivery structures, the biasing members configured to be resiliently expandable and compressible to bias the first and second drug delivery structures away from each other to configure the sulcus implant into a large diameter configuration and permit compression of the sulcus implant into a small diameter configuration.

In various embodiments, the ocular implants comprise an arcuate drug delivery structure 70 configured for implantation into a ciliary sulcus of an eye of a subject, the arcuate drug delivery structure having an outer contour 70C configured for installation in the sulcus, the arcuate drug delivery structure comprising a therapeutic agent configured to treat a condition or disorder of the eye of the subject; a biasing member 71 connected to the arcuate drug delivery structure, the biasing member configured for implantation into a ciliary sulcus of an eye of a subject said biasing member configured to be resiliently expandable and compressible to bias the arcuate drug delivery structure away from one end of the biasing member to configure the sulcus implant into a large diameter configuration and permit compression of the sulcus implant into a small diameter configuration.

In various embodiments, the ocular implants comprise: a resiliently expandable and compressible wire frame 80; and a drug delivery structure comprising panels 81 and 82 joined by posts 83, with the panels and post defining an aperture, wherein a portion of the compressible wire frame is disposed within the aperture.

In some aspects, the ocular implants are configured to resiliently expand until the outside contour meets the sulcus of an eye.

In some aspects, the arcuate drug delivery structure 70 comprises a therapeutic agent.

In certain embodiments, the drug delivery structure 27, 81, 82 comprises a therapeutic agent. In certain aspects, the drug delivery structure is selected from the group consisting of a therapeutic agent, a therapeutic agent disposed in a matrix, an erodible therapeutic agent, and a therapeutic agent in a matrix forming a drug eluting structure, or a combination thereof. In some embodiments, the drug delivery structure 27 is positioned on the posterior surface 15P of the ring 15. In certain aspects, the therapeutic agent is disposed in a matrix forming a drug eluting structure. In some aspects, the drug delivery structure is disposed within the ring or partial ring 15 or the arcuate drug delivery structure 70. In some embodiments, the drug delivery structure or the arcuate drug delivery structure 70 comprise a polymer matrix comprising the therapeutic agent. In certain embodiments, the polymer matrix is bioerodible. In further embodiments, the therapeutic agent comprises one or more of a prostaglandin analogue, an alpha agonist, a ROCK Inhibitor, an adenosine receptor agonists, a carbonic anhydrase inhibitor, an adrenergic and/or cholinergic receptor activating agent, a steroid, an aptamer, a complement factor, an anti-oxidant, an anti-inflammatory agent, an antibody, an anti-proliferative agent, an anti-mitotic agent, or an anti-inflammatory agent. In certain embodiments, the prostaglandin analog comprises bimatoprost.

In various embodiments, the present disclosure provides methods for treating eye conditions or disorders in subjects in need thereof, the methods comprising: providing an ocular implant as described herein; and implanting the ocular implant into the eye of the subject, thereby treating the eye condition or disorder in the subject.

In some aspects, the methods further comprise compressing the ocular implant in an injector, inserting a portion of the injector into the subject's eye, and releasing the ocular implant into the subject's eye. In other aspects, the methods comprise implanting the ocular implant into a posterior chamber and ciliary sulcus of the subject's eye. In other aspects, the methods comprise implanting the ocular implant into a capsular bag of the subject's eye.

In other aspects, the methods further comprise delivering a therapeutic agent from the ocular implant into a tissue of the subject's eye. In certain embodiments, the therapeutic agent is delivered by eluting the therapeutic agent from a matrix comprising the therapeutic agent. In further aspects, the therapeutic agent is a prostaglandin analog. In additional embodiments, the therapeutic agent is bimatoprost.

In some aspects, the eye condition or disorder is selected from the group consisting of age-related macular degeneration, amblyopia (lazy eye), cataracts, color blindness, diabetic retinopathy, dry eye, floaters, glaucoma, pink eye, refractive errors, and retinal detachment, or a combination thereof. In certain aspects, the eye condition or disorder is glaucoma.

In certain embodiments, the subject previously received an intraocular device implanted into a capsular bag in the subject's eye.

In other aspects, the methods further comprise manipulating the device in the eye using a grasping feature 21, 85.

In some aspects, the present disclosure provides ocular implants comprising: a ring configured for implantation in an eye of a patient; and pathways 18 communicating from openings 19 proximate a circumferential surface of the ring to openings 19 proximate an inner wall of the ring.

In other aspects, the present disclosure provides ocular implants comprising: a ring configured for implantation in a posterior chamber of an eye of a patient; and pathways 18 communicating from openings 19 proximate a circumferential surface of the ring to openings 19 proximate an inner wall of the ring. In various aspects, provided herein is a method of treating a condition of an eye of a subject, said method comprising providing an ocular implant comprising: a ring configured for implantation in a capsular bag of an eye of a subject; pathways 18 communicating from openings 19 proximate a circumferential surface of the ring to openings 19 proximate an inner wall of the ring; and implanting the ring into the capsular bag of the eye, such that the pathways allow for flow of aqueous humour from an inner wall of the ring to the openings 19 proximate a circumferential surface of the ring to openings 19 to allow flow of therapeutic agent from the central aperture to an equator of the capsular bag. In some instances, such method can further comprise a drug delivery structure secured to the ring; wherein the drug delivery structure comprises bimatoprost, and the method entails implanting the ocular implant to treat glaucoma. In some instances, such method can further comprise a drug delivery structure secured to the ring; wherein the drug delivery structure comprises a therapeutic agent functional to inhibit proliferation and activity of lens endothelial cells in the equator of the capsular bag and the posterior capsule, and the method entails implanting the ocular implant to inhibit proliferation and activity of lens endothelial cells in the equator of the capsular bag and the posterior capsule.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present disclosure will be obtained by reference to the following detailed description that sets forth illustrative embodiments, in which the principles of the invention are utilized, and the accompanying drawings of which:

FIG. 3 illustrates the drug delivery platform configured for use in the sulcus of the eye, as shown in FIG. 2.

FIG. 4 is a side view of FIG. 3, and FIG. 5 is an anterior perspective view of the drug delivery platform of FIGS. 2 and 3.

FIG. 11 illustrates the drug delivery platform in combination with an implant comprising one or more aqueous humuor flow holes and configured for use in the sulcus of the eye.

FIGS. 12 and 13 are anterior perspective views of the drug delivery platform of FIG. 11.

FIG. 14 illustrates a sulcus lens modified with aqueous fluid apertures.

FIG. 18 is shown as a compressed configuration of FIG. 17.

FIG. 22 depicts a compressed version of the device of FIG. 21.

DETAILED DESCRIPTION OF THE INVENTION

This disclosure provides intraocular devices for implantation into a subject's eye. The devices provided herein can be implanted into various regions of a subject's eye. In various embodiments, provided herein are intraocular devices for implantation into a ciliary sulcus of a subject's eye as described herein.

As used herein, and unless otherwise defined, terms such as "ophthalmic device," "ophthalmic implant," "intraocular device" can be used interchangeably and generally refer to devices that can be implanted into one or more specific location of a subject's (e.g., a human's) eye.

Figure 1:
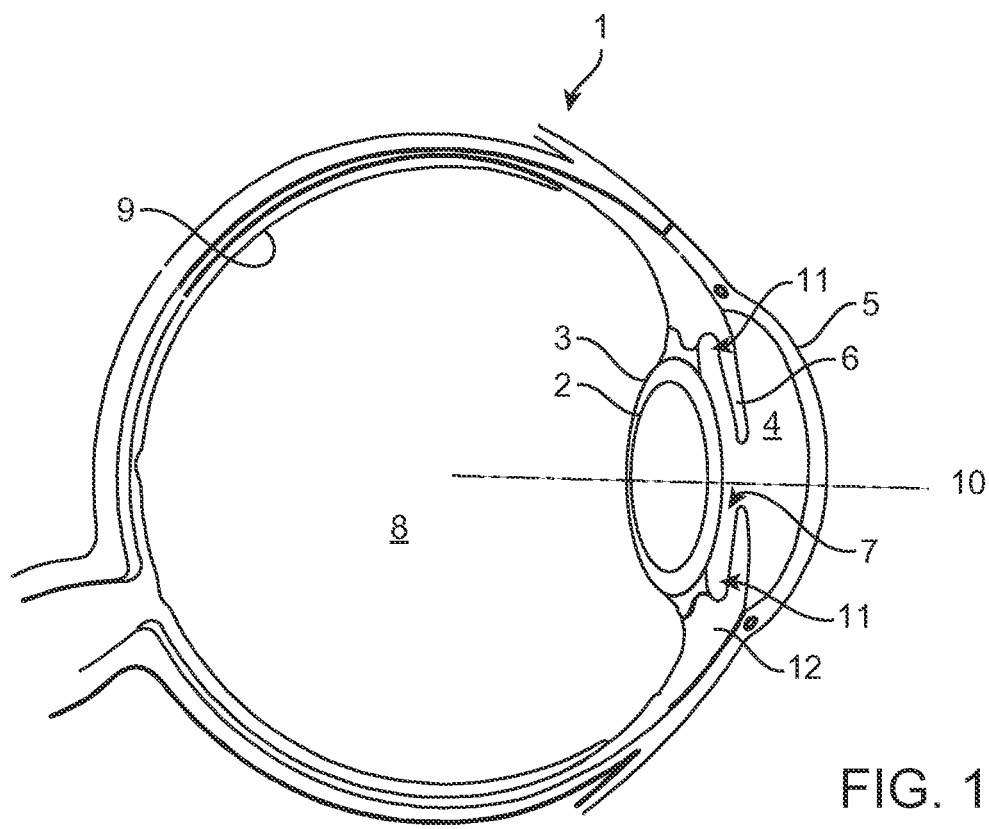
FIGS. 1 and 2 illustrate the environment of use of an intraocular drug delivery system.
Figure 2:
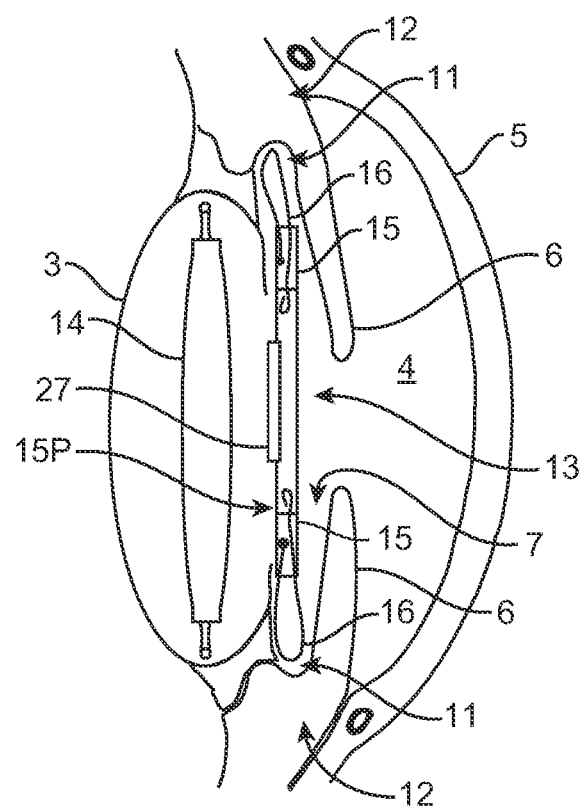

FIGS. 1 and 2 illustrate placement and use of an intraocular drug delivery system or other ocular implant in the eye of a subject. The eye 1 includes a lens 2 and lens capsular bag 3, and the anterior chamber 4 which includes the cornea 5 and iris 6 and aqueous humour filling the space between the cornea and the iris, and the posterior chamber 7 between the iris and the capsular bag. The posterior cavity/vitreous body 8 is the large space between the lens and the retina 9. The natural lens 2 of the eye is characterized by an optical axis 10. The ciliary sulcus 11 is an annular space surrounding the posterior chamber, located between the posterior surface of the iris 6 and the anterior surface of the ciliary body 12. (In the following description of the intraocular implant, the terms posterior and anterior will be used in relation to the anatomy of the eye, in which the cornea is anterior and the retina is posterior). The aqueous humor provides nutrients to the lens and cornea and maintains pressure within the eye. The aqueous humour flows inwardly between the capsular bag/lens and iris, in the sulcus, then flows anteriorly through the aperture of the iris, into the anterior chamber (the open space between the iris and lens and the cornea), then flows radially outwardly between the iris and cornea, where it is drained through structures in the sclera (specifically, the canal of Schlemm and veins in the sclera, not shown).

FIG. 2 illustrates placement of the sulcus implant/drug delivery platform 13 in the eye. In many cases in which the sulcus implant/drug delivery platform is implanted, the subject may have an intraocular lens 14 already in place within the capsular bag, after the natural lens has been removed. In this example, the sulcus implant/drug delivery platform is provided in the form of a ring 15 and is implanted in the posterior chamber 7 and ciliary sulcus 11 alone or in conjunction with another implant. As shown in FIG. 2, the sulcus implant/drug delivery platform 13 is disposed posteriorly to the iris 6 and anteriorly to the ciliary body 12, in the ciliary sulcus in the posterior chamber 7 or, more generally, anteriorly to the anterior capsule of the lens. The sulcus implant/drug delivery platform 13 is held in place with haptics 16 fixed to the sulcus implant/drug delivery platform 13, and configured to engage the tissue of the ciliary sulcus and hold the sulcus implant/drug delivery platform 13 centered over the optical axis 10 of the eye. The haptics are resiliently outwardly biased to accommodate various diameters of the sulcus and expand until they meet the tissue on the border of the sulcus after implantation. A ciliary sulcus can have the following dimensions: 11.55+/−0.38 mm at 45 degrees, 11.99±0.36 mm at 90 degrees, 11.54±0.36 mm at 135 degrees, and 11.32±0.40 mm at 180 degrees, and vertical diameters can be greater than horizontal diameters, with a mean difference between vertical and horizontal diameters of about 0.67±0.26 mm (range, 0.36-1.13 mm).

I. Intraocular Implants

Provided herein are intraocular implants that can comprise one or more U-loop haptics as described herein. In some embodiments, such intraocular implants sulcus implants (e.g., for implantation into a ciliary sulcus of a subject's eye) comprising U-loop haptic(s). In an embodiment, FIG. 3 is an anterior view of the sulcus implant/drug delivery platform of FIG. 2. The drug delivery platform comprises the ring 15, which can be flat like a washer, with a planar anterior surface 15A and a posterior surface 15P (e.g., as shown in FIG. 4), a drug delivery structure 27, and a central aperture 17. In other embodiments, each of the anterior surface 15A and posterior surface 15P may independently not be planar and may comprise a rounded top instead of sharp radii at the ends. The ring 15 includes a radially oriented thru-hole 18, communicating between an opening 19 in the outer circumference of the ring to the inner surface of the ring and an opening 20 in the inner wall of the ring, between the anterior surface of the ring and the posterior surface of the ring, preferably (e.g., in this embodiment) without communication through either the anterior surface of the ring and the posterior surface of the ring. In some embodiments, the radially oriented thru-hole 18 will be replaced by an opening with only an anterior cover (no posterior surface). In this embodiment, the posterior surface will sit flush against the anterior surface of the capsule bag creating a thru-hole that retains the distal tip of the haptic.

The base of the haptic 16B (a "first end") is fixed to the ring in any suitable manner, including mechanically fixing the haptic to the ring, over-molding the haptic with the ring, fusing the haptic to the ring, attaching the haptic to the ring via a heat shrink attachment, attaching the haptic to the ring via an adhesive, or by any other suitable attachment such that it cannot move relative to the ring. The haptic 16 includes a loop portion 16L and has a "free end" or tip 16T (a "second end" or "terminal end") remote from the haptic base 16B. The loop portion extends radially from haptic base 16B junction with the ring and curves back to the ring, where the haptic tip 16T enters the thru-hole 18, and preferably passes through the thru-hole so that the tip is exposed within the central aperture 17. The U-loop or horseshoe-shaped haptic differs from common C-loop and J-loop haptics in that the haptic arcs from the base such that the loop portion extends around an arc sufficient to return to the ring and enter the thru-hole (and, preferably, extend through the through hole and into the central aperture), and differs from plate or loop haptics in that the tip is not immovably fixed to the ring.

The tip can preferably be configured in a manner susceptible to engagement with a Sinskey hook, micro-grasper or other tool. As illustrated, the tip is configured with a grasping feature 21 such as an eyelet, but other configurations, such as a pinhole (sized to accept a Sinskey hook), any serration, flange, barb, wrench flat or other flat surface which may be grasped by a micro-grasper may be used. The tip may be terminated in a blunt end, without a grasping feature, if other suitable grasping tools are available, or if manipulation as describe below is not contemplated.

The distal end 16d of the haptic, including the tip 16T and a short portion proximal to the tip, is configured to be loosely disposed within the radial thru-hole 18, and, correspondingly, the radial thru-hole is configured to loosely receive the distal end 16d of the haptic, including the tip 16T. The haptic distal end, especially that portion disposed within the radial thru-hole, has an anterior-to-posterior dimension (arrows 22 in FIG. 4) and a dimension corresponding to the circumference of the ring (arrows 23 in FIG. 4) sized relative to the anterior-posterior dimension of the radial thru-hole (arrows 24 in FIG. 4) and the dimension corresponding to the circumferential extent of the thru-hole (arrows 25 in FIG. 3) such that the distal end 16d is slidable within the thru-hole, and the distal end 16d may translate radially (or longitudinally) within the thru-hole. The grasping feature 21 may be larger, in one dimension or the other (arrows 26 in FIG. 4), than a corresponding dimension of the radial thru-hole, to prevent the distal tip from escaping the radial thru-hole and becoming unsecured to the ring (the grasping feature preferably acts as a mechanical stop preventing radially outward removal of the haptic from the thru-hole). The eyelet shown, for example, has a diameter greater than the circumferential width, identified by arrow 25, of the thru-hole. This arrangement provides for relief of radially inwardly directed forces applied to the haptic loop by the border of the sulcus. These forces will act to push the haptic tip 16T and distal end 16d into the thru-hole and toward/into the central aperture, avoiding translation of radially inward forces to the ring, which otherwise might deform the ring. The result of radially inwardly directed forces on the haptic is shown in phantom in FIG. 3, with the distal end 16d and grasping feature 21 displaced radially inwardly. Also, because the distal tip is constrained within the thru-hole, the tip cannot be forced into the iris or ciliary body by forces applied by the anatomy or manipulation during implantation or removal, as might a C-Loop or J-Loop haptic, so that the risk of trauma from the tip is minimized or eliminated. Also, as described below, the grasping feature may be used to withdraw the haptic from the sulcus and disengage it from the iris and ciliary body without the need to insert an instrument into the sulcus and pass a tool tip over these structures.

Thus, without the need to insert a tool into the sulcus or the posterior chamber, the haptic may be disengaged from the ciliary sulcus position and elevated beyond the resting plane for easier removal without engaging the iris or surrounding tissues, thus minimizing trauma to collateral tissues. These haptic loops may also assist in placement of the device during primary implantation so that the haptics can be brought in (towards the geometric center of the entire device) and then released (allowed to open into the sulcus) when the ring is positioned properly. The constrained nature of the haptics will also make folding the device for insertion into the eye easier and more reproducible since the haptics will be constrained in a known space and axis and therefore will be easier to compress into an injector and then inject or deposit the device in the eye.

FIG. 4 is a side view of the drug delivery platform of FIGS. 2 and 3, showing the height of the thru-holes and haptic anterior-to-posterior dimension which may closely match. Also shown is the outer circumferential surface 15C. The haptic tip and grasping feature may have an anterior-to-posterior dimension greater than the anterior-to-posterior dimension of the thru-hole. In this side view, the drug delivery structures 27 are shown on the posterior surface 15P of the ring 15. The anterior surface 15A is substantially planar in this illustration, and this is preferred to minimize irritation of the iris. The anterior surface may be smoothly curved, but devoid of projections such as the drug delivery devices and/or compartments shown in other figures. FIG. 5 is an anterior perspective view of the device of FIG. 4. The drug delivery structures may also be positioned in recesses in the anterior surface of the ring, configured with flat anterior surfaces, or surfaces conforming to a smoothly curved anterior surface, and configured to fit within the recesses with the anterior surface of the drug delivery structures not extending anteriorly past the anterior surface of the ring. The angle α of tilt or vault angle of the haptic, relative to the plane of the ring, is preferably about 0° to about 20°, about 0° to about 10°, or 0° to about 5° anteriorly from the base of the haptic.

Figure 10:
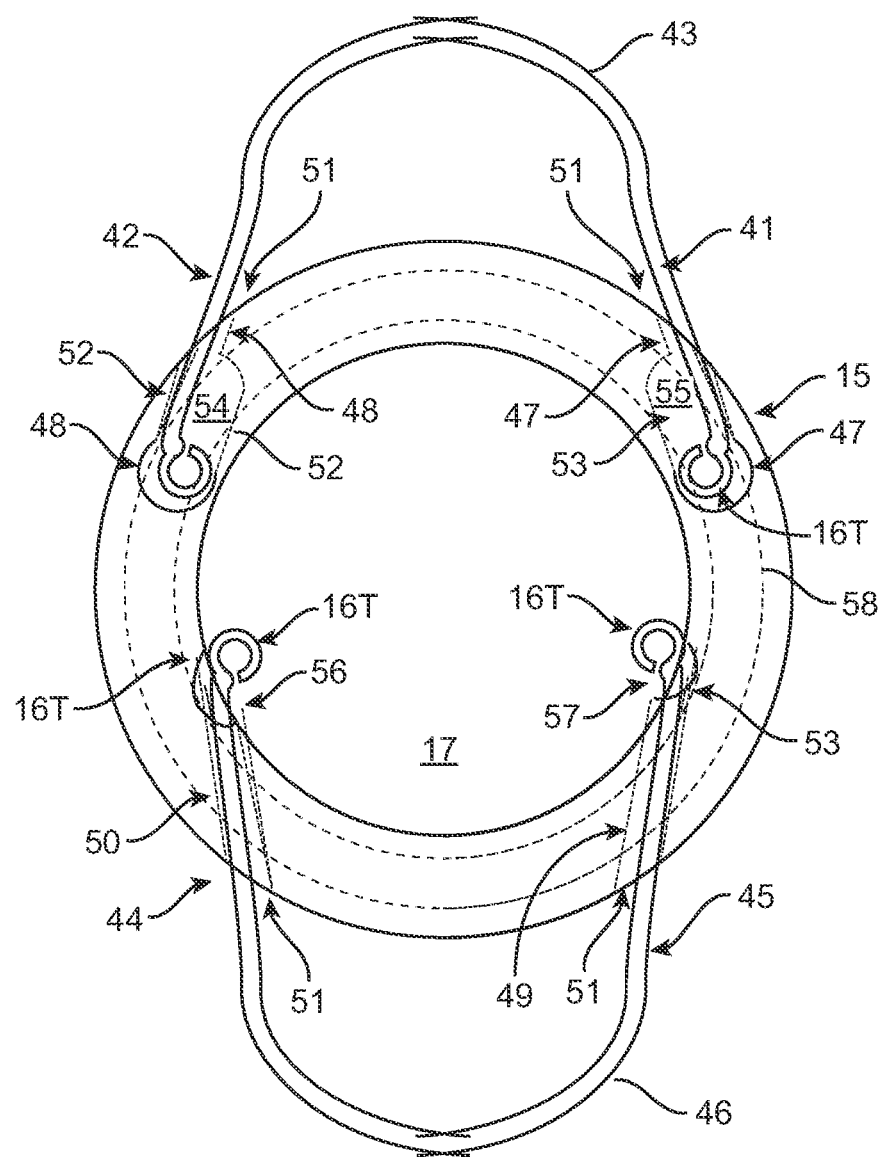
FIG. 10 illustrates variations which may be applied to the devices of FIGS. 2 through 7.

The drug delivery structures may be positioned as shown in FIG. 3, but may also be positioned around the ring, for example in radial alignment or proximity to the haptic base and haptic aperture, or entirely around the posterior surface of the ring (FIG. 10). The drug delivery structures may also function as structural elements to enhance the stability/rigidity of the very thin silicone and might be positioned to enhance the ability of the silicone ring to hold open (that is, minimize deformation away from its unrestrained circular configuration and avoid or minimize "ovalization" after implantation). The base of the haptic might also extend further into the body of the silicone to further enhance the stability of the ring. The base of the haptic shown in FIG. 3 may extend into the ring, extending inside the ring circumferentially, to stabilize the ring. The haptic, when comprised of a material more rigid than the ring, which may preferably be made of silicone, when extended within the ring, serves to increase the rigidity of the assembled haptic and ring.

On the posterior surface 15P, the drug delivery platform may include one or more drug delivery structures 27. The drug delivery structures may be fixed directly to the posterior surface, or they may be disposed in compartments.

The drug delivery structures configured for installation on the ring may be provided as drug depots or masses in the form of blocks, slabs, wafers, etc., comprising a therapeutic agent or a therapeutic agent disposed in a matrix, and may comprise an erodible therapeutic agent or a therapeutic agent in a matrix forming a drug eluting structure.

Figure 6:
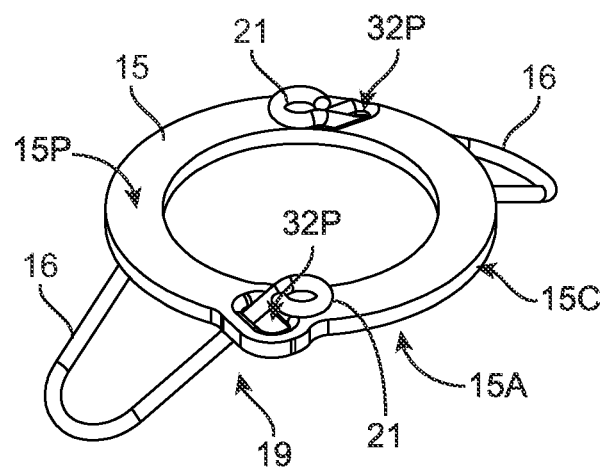
FIGS. 6 and 7 illustrate the drug delivery system configured for posterior access to the haptic tips.
Figure 7:
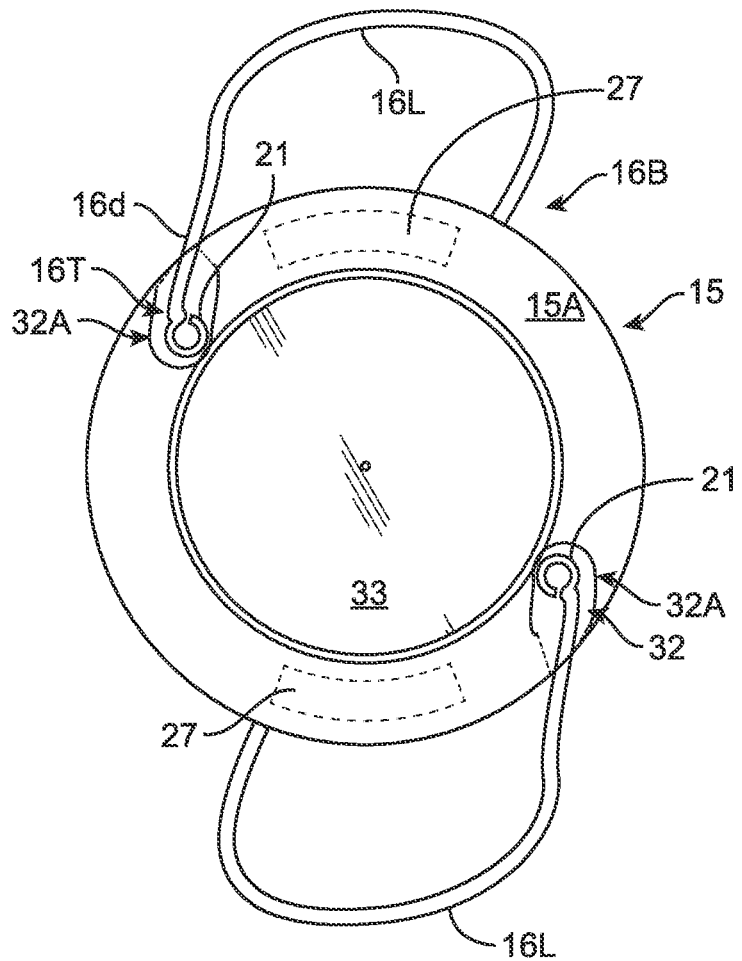
Figure 8:
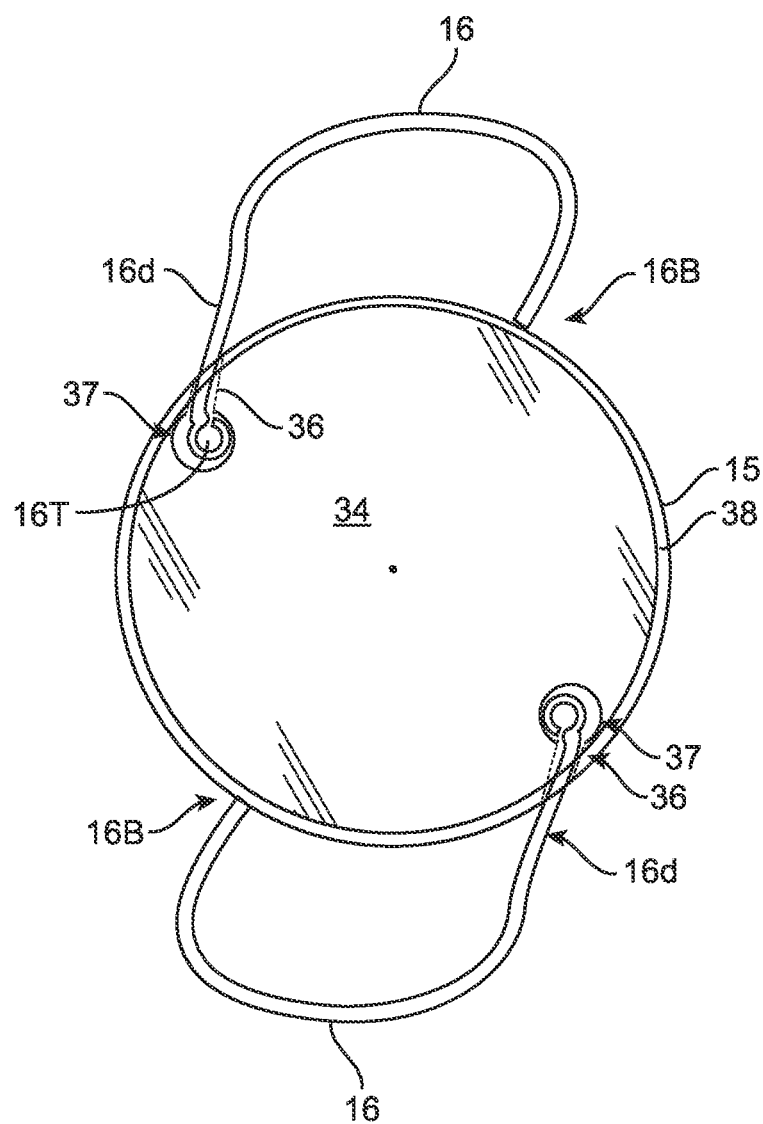
FIG. 8 illustrates a sulcus IOL configured with features of the captive haptic tip.

FIG. 6 illustrates a drug delivery system configured for posterior access to the haptic tips. FIGS. 7 and 8 illustrate the drug delivery system configured for access to the haptic tips. If it is desired to fill the central aperture, for example with a lens or other component, the haptic tip and thru-hole may be configured according to FIGS. 6 and 7, which retain the advantage of minimizing translation of radially compressive forces applied to the haptics by the surrounding tissues of the eye, eliminating the possibility of trauma to the iris from the haptic tip during implantation and removal, and the functionality of grasping the haptic tip in order to release the haptic from the sulcus. In FIG. 6, the thru-hole communicates from an opening 19 in the anterior surface of the ring 15A to a posterior opening 32P in the posterior surface 15A of the ring. The ring can contain a drug delivery structure 27 disposed within the ring. The ring contains a hole 32 into which the haptic tip 16T (at the distal end 16d of the haptic) can extend. The grasping feature 21 may extend posteriorly and radially inward beyond the posterior opening 32P, as shown in FIG. 6, or it may be disposed entirely below the anterior surface of the ring, in the recess at the anterior opening 32A, as shown in FIG. 7. In FIG. 7, the haptic tip 16T and grasping feature 21 are disposed entirely in the recess and entirely posterior to the anterior surface (that is, not protruding forward of the anterior surface of the ring (the bottom of the recess not being considered part of the anterior surface of the ring). The haptics can be in a loop configuration 16L. As shown in FIG. 7, the central aperture may include a lens component 33 to create a lens for implantation in the sulcus, such as an implantable collamer lens (ICL) or to create an IOL for implantation in the capsular bag of a subject.

Figure 9:
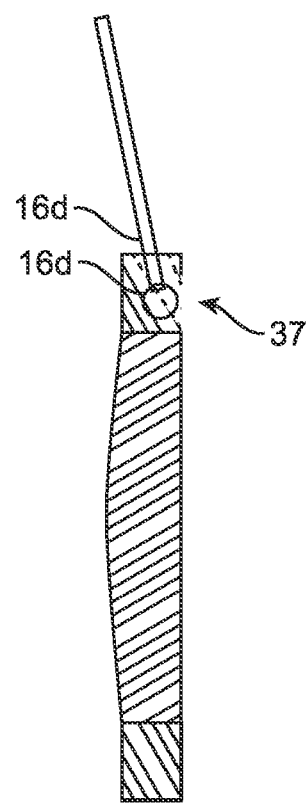
FIG. 9 is a side view illustrating the anterior opening of the thru-hole of the devices of FIGS. 6 through 8.

FIG. 8 illustrates the features of an embodiment of a drug delivery platform comprising a recessed haptic tip in an IOL with a lens 34 and an optional minimal ring 15 used to support the IOL lens. In this figure, the haptic distal end 16d and haptic tip 16T of the haptic 16 and located at the haptic base 16B may be disposed in a thru-hole 36 communicating from the circumference of the lens or frame, or the posterior surface of the lens close to the periphery of the lens, to the opening and recess 37 in the anterior surface 38 of the lens, radially inward of the posterior opening, with the haptic tip disposed entirely in the recess 37 and entirely posterior to the anterior surface (that is, not protruding forward of the anterior optical surface of the lens (the bottom of the recess not being considered part of the anterior optical surface of the lens), so that it cannot contact the iris, but is still accessible to grasping with a hook or grasper, and is still slidable within the thru-hole to alleviate compressive forces applied by surrounding tissue on the haptic. FIG. 9 is a side view of a drug delivery platform or sulcus IOL illustrating the thru-hole which terminates in the opening in the anterior surface of the ring or lens as described in relation to FIGS. 6, 7, and 8. As with the device of FIG. 8, this device comprises an IOL which may be implanted in the sulcus or the capsular bag of a subject.

FIG. 10 illustrates variations which may be applied to the devices of the previous FIGS. 2 through 9. Two different configurations of thru-holes are depicted in FIG. 10. Each end 41 and 42 of the haptic 43, and each end 44 and 45 of the haptic 46 are slidably disposed within chordally oriented (that is, along a secant line of the inner or outer circle of the ring) holes 47, 48, 49 and 50 communicating between openings 51 in the outer circumference of the ring to, or toward, the inner surface of the ring. For haptic 43 (the upper haptic in the illustration), the holes 52 and 53 are blind holes communicating with elongated voids 54 and 55 in the body of the ring, between the anterior surface of the ring and the posterior surface of the ring, without communicating through either the anterior surface of the ring and the posterior surface of the ring, or terminating in a recess in the posterior surface of ring as in FIG. 7. The elongated voids are sized and dimensioned to allow the haptic distal tips 16T to translate within the elongated voids, while each distal tip and the entry port are configured such that the tip cannot be withdrawn from the void. For haptic 46 (the lower haptic in the illustration), the holes 49 and 50 are thru-holes communicating with openings 56 and 57 in the inner wall of the ring, with the bore of each hole disposed between the anterior surface of the ring and the posterior surface of the ring, preferably (in this embodiment) without communicating through either the anterior surface of the ring and the posterior surface of the ring.

In this configuration, both ends of the haptic 44, 45 may be forced inwardly by surrounding tissue, such that, as with the previous figures, the haptics are less likely to injure surrounding tissue in the sulcus. Also, the chordally oriented holes through which the tips translate provide a longer travel for the distal tips, and, for the configuration in which the distal tips extend into the central aperture, travel of the distal tip remains close to the inner wall of the ring, not protruding so far into the central aperture (vis-à-vis the radially oriented thru-holes of FIG. 3).

FIG. 10 also illustrates a configuration of a drug delivery structure 58, which extends entirely around the posterior surface of the ring 15, which may also be applied to devices shown in FIGS. 3-9, 11-14, and 21-27. In other embodiments, the drug delivery structure 58, extends entirely around the anterior surface of the ring 15, which may also be applied to devices shown in FIGS. 3-9, 11-14, and 21-27.

In each device described above, the benefit of trapping the haptic distal end within the thru-holes may be achieved with or without the benefit of the grasping feature which is exposed to facilitate removal of implant. The haptic distal tips 16T, which have a larger cross section than the remainder of the haptic ends 16d, 41, 42, 44, 45 may serve as a locking means to inhibit or prevent complete withdrawal of the haptic second end during implantation. The holes 18, 49, 50, 52 and 53 have a bore with a cross section smaller than the haptic distal tip 16T, so that the distal tips and distal ends can slide inwardly, and expand outwardly, to accommodate forces applied by tissue of the sulcus, but remain constrained within the holes so that they cannot escape the holes.

Further provided herein are intraocular implants that can comprise one or more aqueous humour flow holes as described herein. In some embodiments, such device is a sulcus implant. FIGS. 11 and 12 are anterior views of the sulcus implant/drug delivery platform, wherein the implant can comprise one or more aqueous humuor flow holes 18 and configured for use in the sulcus of the eye. The sulcus implant/drug delivery platform comprises the ring 15, which is preferably flat like a washer, with a planar anterior surface 15A and a posterior surface 15P and a central aperture 17. Drug delivery structures are shown disposed within the ring 27. Haptics of any suitable configuration may be fixed to the outer periphery of the drug delivery platform. The ring 15 includes several aqueous fluid thru-holes 18, communicating between openings 19 proximate to or in the outer circumference or wall of the ring to the inner surface or wall of the ring and an opening 20 proximate to the inner wall of the ring or the anterior surface of the ring near the inner periphery, if, after installation, an inner peripheral zone of the anterior surface will be un-occluded by the iris. The inside openings 20 may also open onto an anterior surface of a lens, in an outer peripheral region of the lens (outside the line of sight) if the implant comprises a sulcus lens or ICL. The ring may have a square radial cross-section, with a flat outer wall, a flat inner wall, and flat anterior and posterior surfaces (a square or rectangular toroid), though one or more surfaces may be rounded, or the ring may have a round or elliptical cross section (a torus).

FIG. 12 is an anterior perspective view of the drug delivery platform of FIG. 11, showing the outside-to-inside thru-holes 18. The thru-holes are depicted as radially oriented thru-holes, but they need not be strictly radially oriented, so long as they communicate from the sulcus to the opening in the iris to allow flow of aqueous humour out of the sulcus and into the anterior chamber of the eye. The thru-holes may be aligned chordally, along secants of the ring, and the thru-holes need not be straight, and may comprise any form of fluid pathway communicating from the exterior of the ring and the ciliary sulcus (when implanted) and the interior of the ring and pupil (when implanted). The fluid pathway may be provided with reticulated open-celled foam, constructed so as to form a network of connected open pores, where the ring is partially or entirely comprised of the reticulated open-celled foam. The fluid pathway may also be provided by a wicking material such as a wicking silicone, a mesh or fibrous material, or a hydrophilic polymer (hydrogel), etc. comprising all or part of the ring.

For implants intended as drug delivery platforms, drug delivery structures 27 may be disposed on the posterior surface of the ring, as shown in FIGS. 12 and 13. The ring shown in FIG. 12 might alternatively be described, in reference to FIG. 13, as a posterior ring 15P and an anterior ring 15A joined by a number of web members or walls 60, separating a number of channels 61 bounded by the webbing on either side of the channel and the anterior and posterior rings on the anterior and posterior boundaries of the channel.

FIG. 14 illustrates a sulcus lens 62 modified with aqueous fluid thru-holes 18 communicating from the outer circumferential surface or wall of the lens. The thru-holes communicate from the openings 19 in the outer edge or circumferential surface of the lens to the anterior openings 20 on the anterior surface of the lens itself. The anterior openings 20 are preferably located in an inner surface region 63 of the anterior surface that is not covered by the iris after implantation as the iris dilates and constricts, as opposed to the outer region of the anterior surface 64 which expected to be covered by the iris, but preferable remain well outside the optical axis and field of view 65 perceptible by the subject. As with the earlier figures, the fluid pathway may be provided with the thru-holes as depicted, or with reticulated open-celled foam, a wicking material, mesh or fibrous material, a hydrophilic polymer (hydrogel), comprising all or part of the inner surface region 63.

The aqueous flow features described with respect to FIGS. 11-14 may be incorporated into other ocular implants which may comprise a mere ring or scaffold for supporting a drug depot, an artificial iris, rings with occluder paddles, an intraocular pressure sensor ring, an optical mask, etc., or, as demonstrated by FIG. 14, an IOL configured for implantation in the posterior chamber and ciliary sulcus or capsular bag.

The application of thru-holes with outlets in the anterior surface of the lens may be applied to other sulcus implants in which the center region of the implant is occupied by a device, such as an occluder or optical mask.

The drug delivery structures may be positioned as shown in FIG. 11, but may also be positioned around the ring, for example in radial alignment or proximity to a haptic base and haptic aperture, or entirely around the posterior surface of the ring. The drug delivery structures may also function as structural elements to enhance the stability/rigidity of the very thin silicone and might be positioned to enhance the ability of the silicone ring to maintain its circular shape (that is, minimize deformation away from its unrestrained circular configuration and avoid or minimize "ovalization" after implantation).

Figure 15:
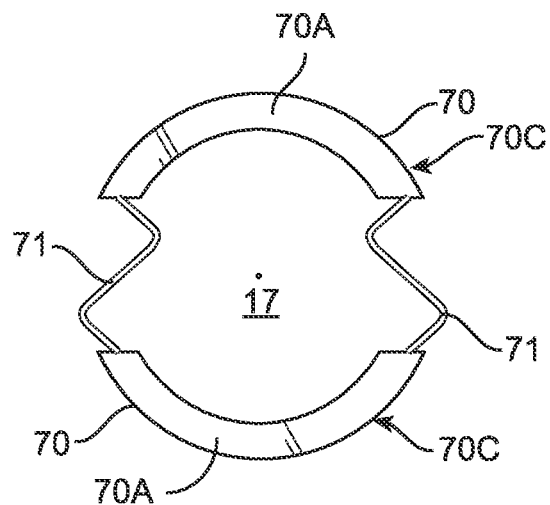
FIG. 15 illustrates a drug delivery sulcus implant configured for use in the sulcus of the eye according to embodiments of this disclosure.

FIG. 15 is an anterior view of a sulcus implant/drug delivery platform as broadly exemplified in FIG. 2. The sulcus implant and/or drug delivery platforms of such embodiments can comprise at least one, and preferably two or more drug delivery structures 70, which are preferably arcuate, with a planar anterior surface 70A and a posterior surface (not shown in FIG. 15). The drug delivery structures 70 are connected by the biasing members 71, leaving a central aperture 17 defined by the inner surfaces of the drug delivery structures and biasing members. The outside contour 70C of the drug delivery structures is preferably arcuate, and more preferably circular, and sized to match the inner curve/circumference of the sulcus of the eye into which it is placed, as it will be biased against the inner circumferential areas of the sulcus such as the ciliary body and ciliary process. The biasing members are configured to fit under the iris, out of the optical field.

Figure 16:
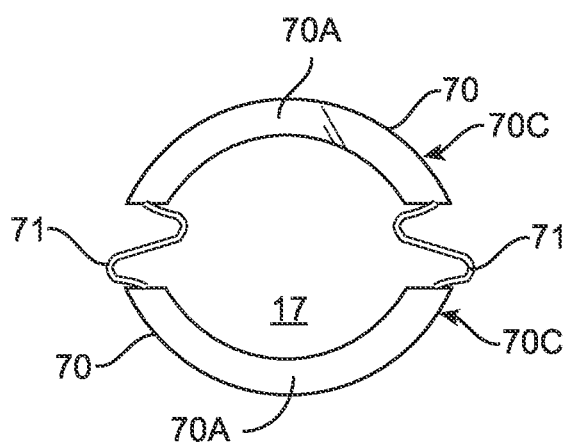
FIG. 16 illustrates a drug delivery sulcus implant shown in FIG. 15 in a compressed configuration according to embodiments of this disclosure.

FIG. 16 illustrates the drug delivery platform of FIG. 15 in a compressed configuration. The device may be compressed toward the compressed small diameter configuration shown in FIG. 16, or expand toward the open, larger, unconstrained large diameter configuration of FIG. 15. The device may be compressed and folded into an injector for delivery into the eye, released into the eye and allowed to resiliently expand until the outside contour meets the sulcus, or compressed to fit the drug delivery structures 70 within the sulcus (depending on the initial state of the device).

The biasing members may be provided in various forms. In an example, and as shown in FIGS. 15 and 16, each biasing member comprises a discrete compression spring connecting the two drug delivery structures show.

Figure 17:
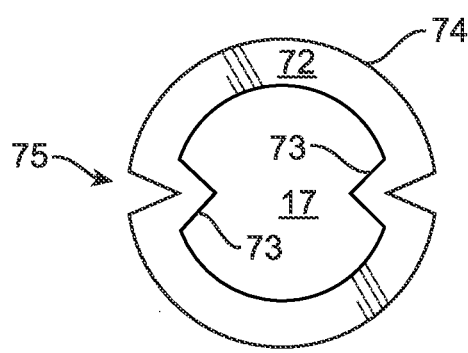
FIGS. 17 and 18 show the drug delivery platform with a biasing member formed integrally with drug delivery structures according to embodiments of this disclosure.

FIG. 17 shows a drug delivery platform 72 with biasing members formed integrally with the drug delivery structures. The biasing members in this device comprise outwardly expansive regions 73 of the device disposed between drug depot regions 74 (though the entire device may comprise a drug depot configured to elute or otherwise deliver a therapeutic agent). Within the device is formed a central aperture 17. The expansive regions are configured as a living hinge joint, defined by a notch 75, and are resiliently biased to open the device to large diameter unconstrained configuration shown in FIG. 17 in which the hinge joints resiliently open to bias the drug depot regions apart from each other, but resiliently compressible to a closed, small diameter constrained configuration shown in FIG. 18. The device may be compressed and folded into an injector for delivery into eye, released into the eye and allowed to resiliently expand until the outside contour meets the sulcus, or compressed to fit the drug depot regions 74 within the sulcus (depending on the initial state of the device).

Figure 18:
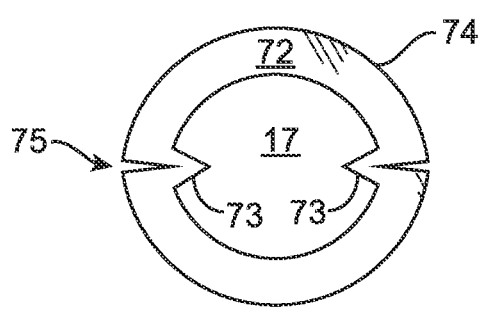

FIG. 18 illustrates the drug delivery platform of FIG. 17 in a compressed configuration. The device may be compressed toward the compressed small diameter configuration shown in FIG. 18, or expand toward the open, larger, unconstrained large diameter configuration of FIG. 17. The device may be compressed and folded into an injector for delivery into eye, released into the eye and allowed to resiliently expand until the outside contour meets the sulcus, or compressed to fit the drug depot regions 74 within the sulcus (e.g., depending on the initial state of the device).

In some embodiments, the arcuate drug delivery structures 70 of FIGS. 15 through 18 are configured to engage the equator or outer border of the ciliary sulcus, while the biasing members 71 are configured to bias the arcuate drug delivery structures 70 and maintain the sulcus implant/drug delivery platform centered over the optical axis 10 of the eye (as shown in FIG. 2). The arcuate drug delivery structures 70 may be limited in circumferential extent so that they do not substantially block the flow path of aqueous humour. The biasing members are preferably of low profile anterior-posterior, again so that they do not substantially block the flow path of aqueous humour, but allow aqueous humour to flow from the sulcus, past the biasing members, and into the anterior chamber.

The devices of the present disclosure, e.g., those shown in FIGS. 15 through 18 can be symmetrical, with two drug delivery structures or drug depot regions, but the devices may be configured with an asymmetrical distribution of drug delivery structures or drug depot regions, and they may be configured with one or several drug delivery structures or drug depot regions.

Some embodiments provided herein (e.g., as shown in FIGS. 15 through 18) are drug delivery intraocular implants comprising one or more outwardly biased drug depots. In some instances, such drug delivery intraocular implants are drug delivery sulcus implants for implantation into a ciliary sulcus or capsular bag of a subject's (e.g., a human's) eye.

Figure 19:
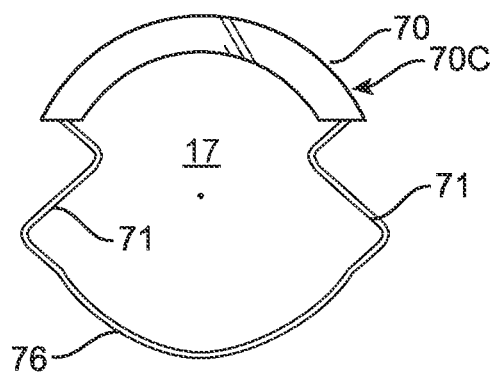
FIG. 19 illustrates a drug delivery platform with a single arcuate drug delivery structure according to embodiments of this disclosure.

FIG. 19 illustrates a drug delivery platform with only a single arcuate drug delivery structures 70 with the arcuate outer contour 70C, e.g., similar to the drug delivery structures of FIG. 15. Biasing members 71 joined by an arcuate connector 76 (which itself may be resilient and function as part of the biasing members) is operable to resiliently bias the single arcuate drug delivery structure 70 away from the arcuate connector 76. The arcuate drug delivery structures 70 combine with the biasing members 71 and arcuate connector 76 to form an inner aperture 17. The devices may also be implanted in the capsular bag, in which case the drug delivery platform of the figures may be inserted into the capsular bag and allowed to resiliently expand within the capsular bag until the drug delivery structures and, if applicable, the biasing members 71 or arcuate connectors 76, impinge on the inside of the capsular bag.

Figure 20:
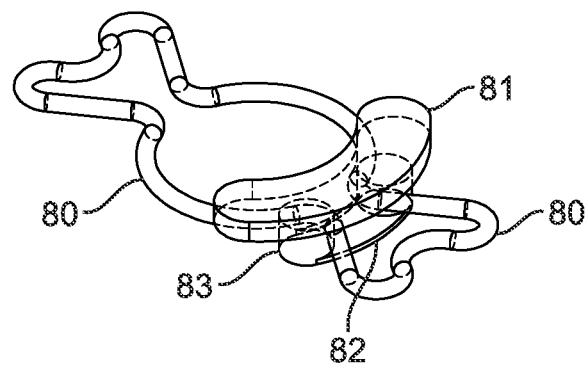
FIG. 20 illustrates a drug delivery platform comprising a drug delivery device with a resiliently expandable and compressible wire frame according to embodiments of this disclosure.

FIG. 20 illustrates a drug delivery platform comprising a drug delivery device with a resiliently expandable and compressible wire frame 80 with a single drug delivery device comprising panels 81 and 82 joined by posts 83, with an aperture between the panels and posts, with a portion of the compressible wire frame disposed within the aperture. The wire frame can comprise any suitable flexible material, such as for example, a compressible polymer or compressible metal.

Figure 21:
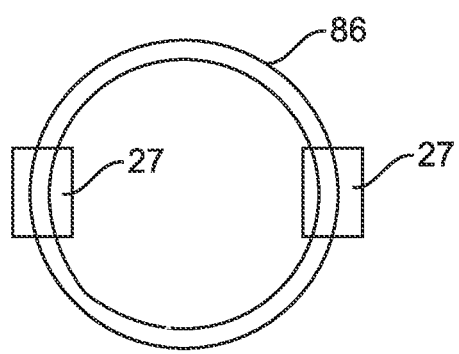
FIGS. 21 and 22 illustrate a drug delivery platform comprising a drug delivery device with a resiliently expandable and compressible ring according to embodiments of this disclosure.
Figure 22:
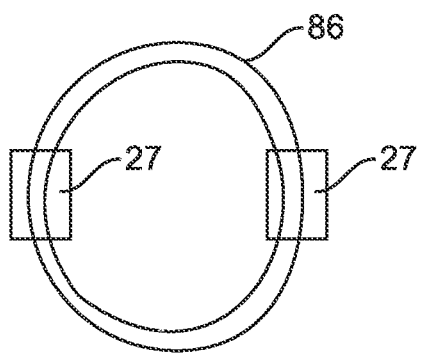

FIGS. 21 and 22 illustrate a drug delivery platform comprising a drug delivery device with a resiliently expandable and compressible ring 84 with drug delivery structures 27 secured to the ring. As with the device of the previous figures, the device may be compressed and folded into an injector for delivery into the eye, released into the eye and allowed to resiliently expand until the outside contour meets the sulcus, or compressed to fit the drug delivery structure 27 (e.g., delivery depots) within the sulcus (depending on the initial state of the device). The compressible ring 84 may be formulated as a drug delivery depot, although in certain embodiments its purpose is to bias the drug delivery structures 27 (e.g., drug depots) outwardly. FIG. 22 illustrates compression of the device shown in FIG. 21, such that it assumes an ovular configuration.

Figure 23:
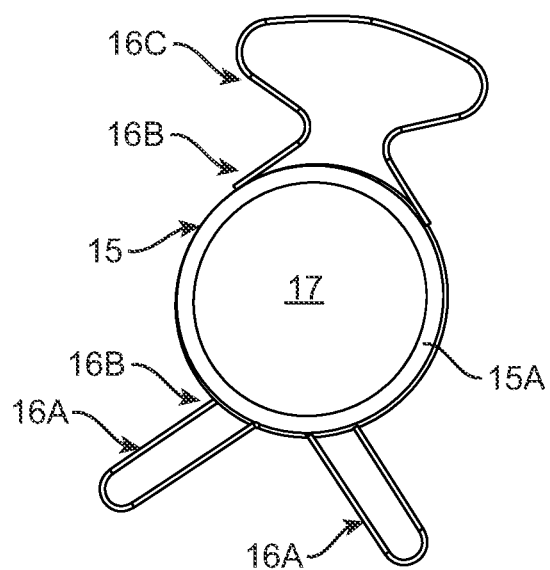
FIG. 23 illustrates a drug delivery platform comprising a closed loop haptic and an A-shaped haptic according to embodiments of this disclosure.
Figure 24:
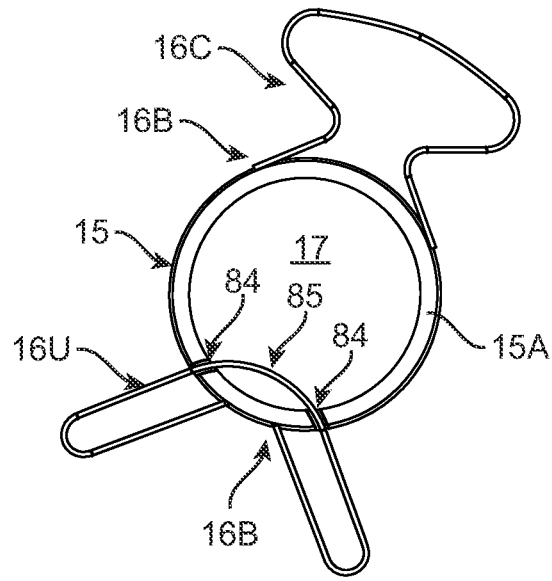
FIG. 24 illustrates a drug delivery platform comprising a closed loop haptic and retention features according to embodiments of this disclosure.
Figure 25:
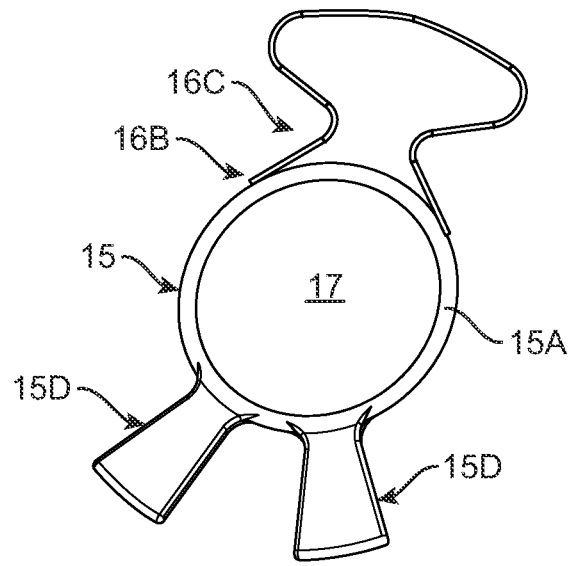
FIG. 25 illustrates a drug delivery platform comprising a closed loop haptic and an A-shaped haptic according to embodiments of this disclosure.
Figure 26:
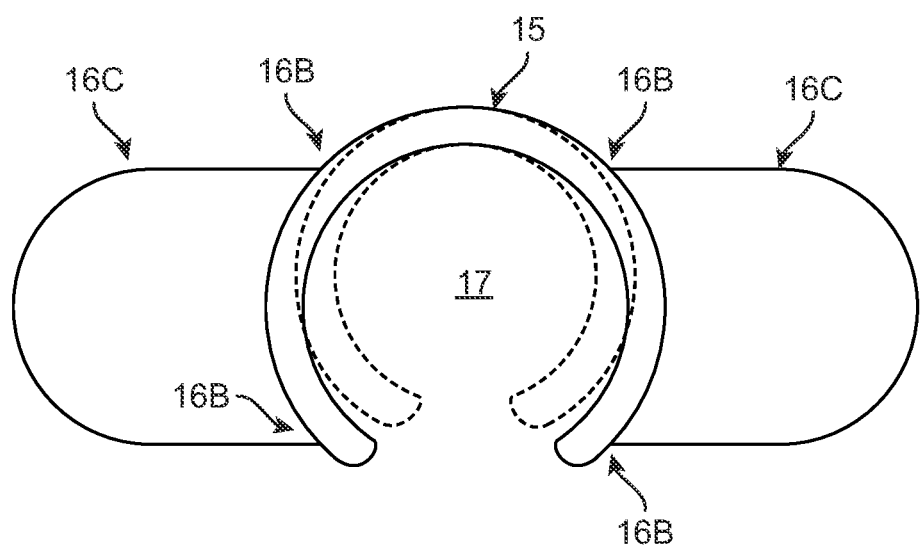
FIG. 26 illustrates a drug delivery platform comprising a plurality of closed loop haptics attached to a compressible, partial ring according to embodiments of this disclosure.

FIGS. 23-26 illustrate additional configurations of drug delivery platforms with flexible configurations that allow for an optimal fit of the device inside the sulcus or capsular bag while providing minimal or no undesired interactions with other tissues of the eye. The individual features of FIGS. 23-25 may also be applied to any of FIGS. 3-22, 26, and 27. The drug delivery platform can comprise a ring (as shown in FIGS. 23-25) or partial ring (as shown in FIG. 26) 15, which can be flat like a washer, with a planter anterior surface 15A and planar posterior surface (not shown in FIGS. 23-26) and a central aperture 17. In other embodiments, the anterior surface 15A or posterior surface may not be planar and may comprise a rounded top or other suitable configuration. In FIG. 23, a closed loop haptic 16C is attached at the haptic bases 16B. In FIG. 26, two closed loop haptics 16C are attached at the haptic bases 16B.

The closed loop haptic 16C can have an hourglass configuration (as in the upper haptics of FIGS. 23, 24, and 25) or other suitable configuration that facilitates stabilization of the drug delivery structure once implanted into the eye of the subject and protection from damage to the eye tissues. The drug delivery device can have a single closed loop haptic or a plurality of closed loop haptics. Additional haptics can also be attached to the ring in other embodiments. As shown in FIGS. 23 and 24, a second set of haptics (16A in FIGS. 23 and 16U in FIG. 24) can be attached to the ring 15 at haptic bases 16B. These additional haptics can take various forms, including a U-shaped configuration (as in the lower haptic of FIG. 24), an A-shaped configuration (as in the lower haptic of FIG. 23), or other suitable configuration as shown in FIGS. 3 through 10. Each of the closed loop haptics and other haptics 16A, 16U can be attached at a haptic base 16B in any suitable way, including mechanically fixing the haptic to the ring, over-molding the haptic with the ring, fusing the haptic to the ring, attaching the haptic to the ring via a heat shrink attachment, attaching the haptic to the ring via an adhesive, or by any other suitable attachment. Alternatively, the closed loop haptics 16C and/or other haptics 16A, 16U may also be flexibly connected to the ring 15 according to any of the methods described for FIGS. 3 through 10.

As shown in FIG. 24, haptics 16U can also pass through holes or channels 84 in the ring 15 such that the haptic 16U extends into the central aperture 17 of the device and forms a grasping feature 85.

As shown in FIG. 25, the drug delivery device can comprise extensions of the ring 15 to form one or more retention features 15D. The retention features can comprise the same or different material as the ring. The retention features 15D may be continuous with the ring or attached to the ring in any suitable manner.

The partial ring 15 in FIG. 26 is compressible under the application of force. The result of such compression on the device is shown in phantom in FIG. 26.

As with other devices of the present disclosure, the devices of FIGS. 23-26 can include a drug delivery structure, which can be disposed on the anterior surface 15A, posterior surface, incorporated into the ring, or may be disposed in separate compartments within the device.

Figure 27:
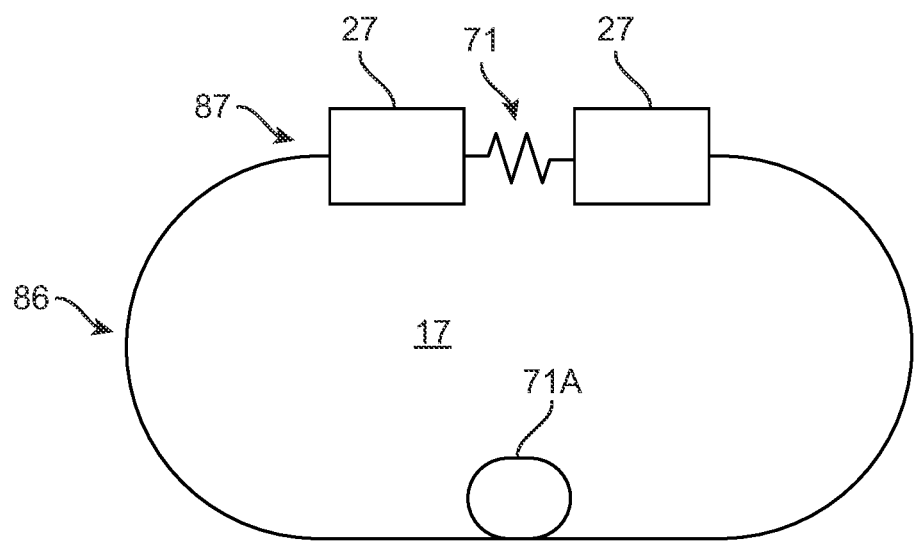
FIG. 27 shows a drug delivery platform with a biasing member formed integrally with drug delivery structures according to embodiments of this disclosure.

The device of FIG. 27 comprises a flexible and compressible ring structure 86 forming a central aperture 17. The device also contains one or more drug delivery structures 27 (attaching to the ring structure at the ring structure base 87), a loop 71A that facilitates stabilizing the ring structure, and a biasing member 71 disposed between the drug delivery structures 27. The ring structure can be composed of the same material as found in any of the haptics described in the present disclosure.

In various embodiments of the present disclosure, the haptics 16L, 16, 16C, 16A, 16U are connected to the rings or partial rings 15, 83, 86 by mechanically fixing the haptic(s) to the rings or partial rings, over-molding the haptics with the ring or partial ring, fusing the haptic(s) to the ring or partial ring, attaching the haptic(s) to the ring or partial ring via a heat shrink attachment, attaching the haptic(s) to the ring or partial ring via an adhesive, or by any other suitable attachment. Such attachments include those depicted in FIGS. 3-9, 23-26.

Suitable materials for the haptics 16L, 16, 16C, 16A, 16U, 43, 46 of the present disclosure include biocompatible materials, including polymeric materials, such as for example, a polymethyl methacrylate (PMMA), polyvinylidene difluoride (PVDF), Polypropylene (PP) and Polyethersulfone (PES) or any combination thereof. Suitable materials for the rings or partial rings 15, 83, 86 of the present disclosure include biocompatible materials, including polymeric materials, such as for example a silicone, an acrylic, hydroxyethyl methacrylate (HEMA), polyethylmethacrylate (PEMA), polyethylacrylate (PEA), and combinations thereof.

In various embodiments, the ocular implants of the present disclosure comprise a ring or partial ring 15 comprising a first material and configured for implantation into an eye of a subject, the ring or partial ring characterized by an outer circumferential surface, an inner wall, and a central aperture 17 and a closed loop haptic 16, 16C, 16L, 43, 46 comprising a second material and attached to the ring or partial ring at a haptic first end 16d, 41, 45 and at a haptic second end 16d, 42, 44, wherein the first material and the second material have different chemical compositions and the ring or partial ring is more rigid than the closed loop haptic.

In various aspects, a force applied to the ocular implants of the present disclosure (e.g., as shown in FIGS. 3-10 and 23-26) is sufficient to deform the haptic (e.g., a closed loop haptic 16, 16C, 16L, 43, 46) but not the ring or partial ring. Generally, at the conditions present in the eye following implantation, the ring or partial ring retains its shape and the closed loop haptic deforms. In some aspects, at an applied force of 100 mN, the ring or partial ring retains its shape and the closed loop haptic deforms. In other aspects, at an applied force of 80 mN, the ring or partial ring retains its shape and the closed loop haptic deforms. In further aspects, at an applied force of 60 mN, the ring or partial ring retains its shape and the closed loop haptic deforms. In other aspects, at an applied force of 50 mN, the ring or partial ring retains its shape and the closed loop haptic deforms. In some aspects, at an applied force of 40 mN, the ring or partial ring retains its shape and the closed loop haptic deforms. In further aspects, at an applied force of 30 mN, the ring or partial ring retains its shape and the closed loop haptic deforms. In other aspects, at an applied force of 20 mN, the ring or partial ring retains its shape and the closed loop haptic deforms. In other aspects, at an applied force of 10 mN, the ring or partial ring retains its shape and the closed loop haptic deforms. In some aspects, at an applied force of 5 mN, the ring or partial ring retains its shape and the closed loop haptic deforms.

The drug delivery devices according to FIGS. 3-27 can be configured in a variety of ways to facilitate delivery of therapeutics to the tissues of the eye. Generally, and as further described herein, the one or more drug delivery structures 27, 58, 70, 81 may be provided as drug depots or masses in the form of blocks, slabs, wafers, etc. comprising a therapeutic agent or a therapeutic agent disposed in a matrix, and may comprise an erodible therapeutic agent or a therapeutic agent in a matrix forming a drug eluting structure. Each of the devices described herein for implantation in the posterior chamber and sulcus are also suitable for implantation in the capsular bag. The devices of the present disclosure are configured to provide therapeutic agents to the capsular bag in the equator of the capsular bag or the posterior chamber and sulcus. For example, therapeutic agents functional to inhibit proliferation and activity of lens endothelial cells and formation of posterior capsular opacification (e.g., cytoskeletal drugs, latrunculin, anti-VEGF, etc.).

For each of the devices described herein and depicted in FIGS. 3-27, the drug delivery structures 27, 58, 70, 81 can be disposed on or within the posterior surface 15P, on or within the anterior surface 15A, or a combination thereof. The drug delivery structures may be fixed directly to the posterior and/or anterior surface, they may be disposed in compartments fixed to the posterior surface, or they may be otherwise incorporated into the device. The rings or partial rings 15, 83, 86 themselves may comprise a drug delivery structure 27, 58, 70, 81, for example being comprised of a therapeutic agent within a silicone matrix.

II. Methods for Implanting and Manipulating Ocular Implants

Intraocular implants of the present disclosure and as illustrated in FIGS. 3-27 can be used for various applications in a subject's eye. In some embodiments, the drug delivery platform of such devices described herein may be used in a method for intraocular delivery of therapeutic agent into an eye of a subject, into the ciliary sulcus. In various aspects, the drug delivery devices of the present disclosure comprise closed loop haptics, or more specifically U-loop haptics. Using the various embodiments of the present disclosure, a surgeon can insert the drug delivery device of the present disclosure into the eye of a subject and place the haptics under the iris and center the ring over the capsular bag and lens.

In some aspects, the devices of the present disclosure comprise an IOL. For example, such devices comprising an IOL are shown in FIGS. 7 and 8, or as an IOL disposed within the central aperture 17 and surrounded by any ring 15 of the present disclosure, including for the devices shown in FIGS. 3-6, 10-14, and 23-25). In various embodiments, the devices of the present disclosure can be implanted into a subject's eye where an IOL device was previously implanted (e.g., as a device implanted in the capsular bag) or into a subject's eye still containing the natural lens and having an intact capsular bag.

The devices of the present disclosure as shown in FIGS. 3-27 can be implanted such that the devices may or may not be centered on the optical axis of the eye. Thereafter, either intraoperatively or long after implantation, the surgeon may remove the drug delivery platform by inserting a tip grasping tool through an incision into the eye (at the base of the cornea, "clear cornea" or "limbal entry point" along the corneal limbus or even "scleral entry point"), such as a Sinskey hook or micro-grasper under the cornea, from a point opposite the tip to be grasped or from a circumferentially displaced entry point (around the edge of the cornea) from the tip to be grasped so that the tool can pull the tip radially inward, then grasp the tip and gently pull it radially inward, across the aperture, to disengage the haptic from the sulcus and move it to a position anterior to the iris, repeat the process from the other side of the cornea (the other side of the corneal limbus (the border of the cornea and sclera) or the other side of the anterior chamber) to release the second haptic tip, and remove the drug delivery platform through the incision under the cornea. This removal procedure may be accomplished without inserting a tool in the sulcus or grasping and directly manipulating the loop portion of the haptic or exposing the iris to the haptic tip or allowing the haptic tip to be exposed within the sulcus.

Although described in relation to a drug delivery platform, the modified haptic structures described above and as shown in FIGS. 3-10, 23-26 may be incorporated into other ocular implants which may comprise a mere ring or scaffold for supporting a drug depot, an artificial iris, rings with occluder paddles, an intraocular pressure sensor ring, an optical mask, etc., or, as demonstrated by FIGS. 7 and 8, an IOL configured for implantation in the posterior chamber and ciliary sulcus. Also, the devices described for implantation in the posterior chamber and sulcus may also be implanted in the capsular bag, to achieve the benefits of the captured haptic, or the stress relieving aspect of capturing the haptic in the holes, or the benefits of grasping the haptic tip for adjustment and removal, in combination or alone.

In various aspects of the present disclosure, the haptic tips 16T can preferably be configured in a manner susceptible to engagement with a Sinskey hook, micro-grasper or other tool. In additional to the haptic tips 16T incorporating a grasping feature 21, additional devices of the present disclosure incorporate a grasping feature 85. As illustrated in FIGS. 3, 5, 6, 10, and 24, the haptic tips 16T can be configured with a grasping feature 21, 85 such as an eyelet, or other configurations, such as a pinhole (sized to accept a Sinskey hook), any serration, flange, barb, wrench flat or other flat surface which may be grasped by a micro-grasper may be used. For the devices shown in FIGS. 3-10, the tip may be terminated in a blunt end, without a grasping feature, if other suitable grasping tools are available, or if manipulation as describe below is not contemplated. Without the need to insert a tool into the sulcus or the posterior chamber, the haptic may be disengaged from the ciliary sulcus position and elevated beyond the resting plane for easier removal without engaging the iris or surrounding tissues, thus minimizing trauma to collateral tissues. These haptics 16L, 16, 16C, 16A, 16U, 43, 46 (including the haptic loops 16L, 16, 16C, 43, 46) may also assist in placement of the device during primary implantation so that the haptics can be brought in (towards the geometric center of the entire device) and then released (allowed to open into the sulcus) when the ring is positioned properly. In various aspects, the constrained nature of the haptics (e.g., closed loop haptics of the present disclosure) will also make folding the device for insertion into the eye easier and more reproducible since the haptics will be constrained in a known space and axis and therefore will be easier to compress into an injector and then inject or deposit the device in the eye.

III. Methods of Treating Subjects Using the Ocular Implants

The drug delivery devices of the present disclosure and as shown in FIGS. 3-27 may be used in a method for intraocular delivery of a therapeutic agent into an eye of a subject, including into the ciliary sulcus or the capsular bag of the subject. For treatment of glaucoma, for example, the therapeutic agent in the drug delivery structure 27, 58, 81 may be a therapeutic agent effective to reduce intraocular pressure, such as bimatoprost. In some aspects, a surgeon will insert any of the devices of the present disclosure (e.g., as shown in FIGS. 3-27) into the posterior chamber, positioned between the iris and the capsular bag, with the anterior surface toward the iris and the posterior surface facing the capsular bag, and any haptics used extending into the ciliary sulcus.

For each of the embodiments described herein, including as shown in FIGS. 3-27, the drug delivery device can be configured to deliver various therapeutic agents for the treatment of a condition or disorder in a subject in need thereof. Treatment includes any amelioration of a condition or disorder or improvement in any symptom thereof (subjectively or objectively). The devices of the present disclosure can be used to treat age-related macular degeneration, amblyopia (lazy eye), cataracts, color blindness, diabetic retinopathy, dry eye, floaters, glaucoma, pink eye, refractive errors, retinal detachment, and any combination thereof. In some embodiments, therapeutic agents can include bimatoprost, brimonidine, latanoprost, timolol, pilocarpine, brinzolamide and other drugs in the general categories of beta blockers, alpha agonists, ROCK Inhibitors, adenosine receptor agonists, carbonic anhydrase inhibitors, adrenergic and cholinergic receptor activating agents, and prostaglandin analogues may be incorporated into the drug delivery devices to treat glaucoma. Aflibercept, bevacizumab, pegaptanib, ranibizumab, steroids, and aptamers may be incorporated into the drug delivery devices to treat wet macular degeneration. Complement factors, anti-oxidants and anti-inflammatory agents may be incorporated into the drug delivery devices to treat dry macular degeneration. Methotrexate, antibodies, dexamethasone, triamcinolone, and other steroid agents may be incorporated into the drug delivery devices to treat uveitis. Anti-proliferative agents, anti-mitotic agents, anti-inflammatory agents, and other medications that would inhibit the spread of lens epithelial cells may be incorporated into the drug delivery devices to treat posterior capsular opacification. Antibiotics such as fluoroquinolones, non-steroidal agents such as ketorolac, and steroids such as prednisolones may be incorporated into the drug delivery devices for post-op management after cataract surgery to treat infection and inflammation.

Further provided herein are methods of treating a subject using the drug delivery intraocular implants comprising outwardly biased drug depots, for example as shown in FIGS. 21, 22, and 27. Further embodiments of the present disclosure (e.g., any of FIGS. 3-20, 23-26) can be modified to include one or more outwardly biased drug depots. As disclosed herein, such drug delivery intraocular implants can be drug delivery sulcus implants for implantation into a ciliary sulcus or capsular bag of a subject's eye. In various embodiments, and in use, the sulcus implant and/or drug delivery platform comprising such outwardly biased drug depots and as illustrated in the FIGS. 21, 22, and 27 herein (or other embodiments as modified to incorporate a drug depot) may be used in a method for intraocular delivery of a therapeutic agent into an eye of a subject by inserting the device into the anterior chamber of the eye, with the drug delivery structures inserted into the ciliary sulcus, and allowing the device to resiliently expand. Upon release into the anterior chamber, biasing members will resiliently expand circumferentially to push the drug delivery structures outwardly within the sulcus until they impinge upon anatomical structures in the sulcus angle.

Provided herein are methods of using intraocular implants comprising one or more aqueous humour flow holes (e.g., as shown in FIGS. 11-14 or as incorporated into any of FIGS. 3-10 and 15-17). In various cases, such implants are sulcus implants for implantation into a ciliary sulcus or in the capsular bag of a subject's eye. After implantation, the fluid pathways will allow aqueous humour through the ring, preventing a buildup of fluid in the sulcus and posterior chamber. If implanted in the capsular bag, such that the pathways allow for flow of fluid from an inner wall of the ring to the openings 19 proximate a circumferential surface of the ring, therapeutic agent may be delivered from the central aperture to an equator of the capsular bag.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

What is claimed is:

1. An ocular implant configured for implantation into an eye of a subject, the ocular implant comprising:
    a ring configured for implantation into the eye of the subject, the ring including an outer circumferential surface, an inner wall, and a central aperture;
    a haptic connected to the ring at a haptic first end and a haptic second end;
    wherein the ring comprises a hole communicating from an opening in the outer circumferential surface toward the inner wall; and
    the haptic second end is slidably disposed within the hole, whereby the haptic is deformable by forces applied by tissues into which the ocular implant is implanted to force the haptic second end into the hole.

2. The ocular implant of claim 1, wherein the haptic second end comprises a haptic distal tip having a larger cross section than a remainder of the haptic second end.

3. The ocular implant of claim 1, further comprising a lens disposed within the central aperture.

4. The ocular implant of claim 1, wherein the haptic second end comprises a haptic distal tip having a larger cross section than a remainder of the haptic second end and the hole has a bore with a cross section smaller than the haptic distal tip, whereby the haptic second end is inhibited or prevented from removal from the hole.

5. The ocular implant of claim 1, further comprising a grasping feature disposed on the haptic second end, the grasping feature configured for engagement of a grasping tool.

6. The ocular implant of claim 1, wherein the hole communicating from the opening in the outer circumferential surface toward the inner wall is a through hole communication to an opening in the inner wall of the ring, and the haptic second end comprises a haptic distal tip having a larger cross section than a remainder of the haptic second end and the haptic distal tip is disposed in the central aperture.

7. The ocular implant of claim 1, wherein the haptic first end comprises a haptic distal tip having a larger cross section than a remainder of the haptic first end.

8. The ocular implant of claim 1, wherein the haptic first end comprises a haptic distal tip having a larger cross section than a remainder of the haptic first end, and the hole has a bore with a cross section smaller than the haptic distal tip, whereby the haptic first end is inhibited or prevented from removal from the hole.

9. The ocular implant of claim 1, wherein the hole is a first hole, the ring further comprising a second hole communicating from a second opening in the outer circumferential surface toward the inner wall, wherein the haptic first end is slidably disposed within the second hole, the haptic is deformable by the forces applied by the tissues into which the ocular implant is implanted to force the haptic first end into the second hole.

10. The ocular implant of claim 1, wherein the ocular implant is configured for implantation in a posterior chamber and a ciliary sulcus of the eye of the subject, the ring configured for implantation in the posterior chamber of the eye of the subject.

11. The ocular implant of claim 1, wherein the ring is configured for implantation into a capsular bag of the eye of the subject.

12. The ocular implant of claim 1, wherein the haptic forms a closed loop between the haptic first end and the haptic second end.

13. The ocular implant of claim 1, further comprising a drug delivery structure.

14. The ocular implant of claim 13, wherein the drug delivery structure comprises a therapeutic agent.

15. The ocular implant of claim 14, wherein the therapeutic agent is disposed in a polymer matrix.

16. The ocular implant of claim 15, wherein the drug delivery structure is coupled to the ring.

17. The ocular implant of claim 14, wherein the therapeutic agent comprises one or more of a prostaglandin analogue, an alpha agonist, a ROCK Inhibitor, an adenosine receptor agonists, a carbonic anhydrase inhibitor, an adrenergic and/or cholinergic receptor activating agent, a steroid, an aptamer, a complement factor, an anti-oxidant, an anti-inflammatory agent, an antibody, an anti-proliferative agent, an anti-mitotic agent, or an anti-inflammatory agent.

18. The ocular implant of claim 14, wherein the therapeutic agent comprises bimatoprost.

19. The ocular implant of claim 13, wherein the drug delivery structure is coupled to a posterior surface of the ring.

20. The ocular implant of claim 13, wherein the drug delivery structure comprises a pair of arcuate structures coupled to the ring.

* * * * *

UNITED STATES PATENT AND TRADEMARK OFFICE
CERTIFICATE OF CORRECTION

PATENT NO. : 11,806,227 B2
APPLICATION NO. : 17/954631
DATED : November 7, 2023
INVENTOR(S) : Craig Alan Cable, II et al.

Page 1 of 1

It is certified that error appears in the above-identified patent and that said Letters Patent is hereby corrected as shown below:

In the Claims

In Claim 9, Column 22, Line 37, insert --whereby-- after "hole".

Signed and Sealed this
Twenty-sixth Day of November, 2024

Katherine Kelly Vidal
*Director of the United States Patent and Trademark Office*